(12) United States Patent
Graf et al.

(10) Patent No.: US 11,730,567 B2
(45) Date of Patent: Aug. 22, 2023

(54) ORTHODONTIC APPARATUS AND METHOD FOR PRODUCING AN ORTHODONTIC APPARATUS

(71) Applicant: Digital Smile GmbH, Oberegg (CH)

(72) Inventors: Simon Graf, Bern (CH); Roland Kiss, Au (CH); Mark Kabashi, Au (CH)

(73) Assignee: Digital Smile GMBH, Oberegg (CH)

( * ) Notice: Subject to any disclaimer, the term of this patent is extended or adjusted under 35 U.S.C. 154(b) by 0 days.

(21) Appl. No.: 15/311,301

(22) PCT Filed: May 20, 2015

(86) PCT No.: PCT/EP2015/061156
§ 371 (c)(1),
(2) Date: Nov. 15, 2016

(87) PCT Pub. No.: WO2015/177235
PCT Pub. Date: Nov. 26, 2015

(65) Prior Publication Data
US 2017/0079747 A1    Mar. 23, 2017

(30) Foreign Application Priority Data

May 23, 2014   (CH) ..................................... 00787/14

(51) Int. Cl.
*A61C 7/10*       (2006.01)
*B33Y 10/00*      (2015.01)
(Continued)

(52) U.S. Cl.
CPC ................ *A61C 7/002* (2013.01); *A61C 7/08* (2013.01); *A61C 7/10* (2013.01); *B33Y 10/00* (2014.12); *B33Y 80/00* (2014.12)

(58) Field of Classification Search
CPC .. A61C 7/002; A61C 7/12; A61C 7/10; A61C 7/08; A61C 7/20; B33Y 10/00; B33Y 80/00
(Continued)

(56) References Cited

U.S. PATENT DOCUMENTS 3,460,253 A * 8/1969 Henri ........................ A61C 7/10
433/172
4,482,318 A * 11/1984 Forster ..................... A61C 7/10
433/7
(Continued)

FOREIGN PATENT DOCUMENTS

CA  WO 2014008583 A1 *  1/2014  ............. A61C 7/002
DE          3213489      *  9/1983  ............... A61C 7/10
(Continued)

OTHER PUBLICATIONS

Translation of abstract for DE 3213489 (Year: 1983).*
International Search Report issued in PCT/EP2015/061156 dated Jul. 23, 2015, 2 pages.

*Primary Examiner* — Heidi M Eide
(74) *Attorney, Agent, or Firm* — Pearne & Gordon LLP

(57) ABSTRACT

An orthodontic apparatus (1; 10) is designed with at least one orthodontically effective element (4; 12) and at least one holding element (5; 13) for holding the apparatus (1; 10) on the jaw, whereby the apparatus (1; 10) is designed in one piece. In a method for producing an orthodontic apparatus, an electronic data set is produced for a three-dimensional model (2) of a jaw to which the apparatus is supposed to be attached. Further, a virtual positioning of one or more orthodontic elements (4; 12) of the apparatus on jaw model (2) takes place. An electronic data set of a three-dimensional model (3; 11) of the apparatus is subsequently produced. The (Continued)

apparatus (1; 10) is then produced by an additive and/or removal production method according to the data set of the apparatus model.

13 Claims, 2 Drawing Sheets

(51) Int. Cl.
  *B33Y 80/00* (2015.01)
  *A61C 7/00* (2006.01)
  *A61C 7/08* (2006.01)
(58) Field of Classification Search
  USPC .............................................................. 433/7
  See application file for complete search history.

(56) References Cited

U.S. PATENT DOCUMENTS

| | | | | |
|---|---|---|---|---|
| 4,976,614 A * | 12/1990 | Tepper | ...................... | A61C 7/00 433/18 |
| 5,242,304 A * | 9/1993 | Truax | ...................... | A61C 7/00 433/177 |
| 5,376,001 A * | 12/1994 | Tepper | ...................... | A61C 7/00 433/6 |
| 5,775,898 A * | 7/1998 | Schellino | ................. | A61C 7/10 433/7 |
| 6,220,856 B1 * | 4/2001 | Carano | .................... | A61C 7/10 433/7 |
| 6,227,851 B1 * | 5/2001 | Chishti | ................... | A61C 7/08 433/24 |
| 6,766,802 B1 * | 7/2004 | Keropian | ................ | A61F 5/566 128/848 |
| 7,476,100 B2 * | 1/2009 | Kuo | ......................... | A61C 7/00 433/6 |
| 7,661,955 B2 * | 2/2010 | Da Cruz | ................. | A61C 7/10 433/18 |
| 7,735,542 B2 * | 6/2010 | Marshall | ................ | A61C 5/77 164/35 |
| 8,313,327 B1 * | 11/2012 | Won | ......................... | A61C 7/10 433/23 |
| 8,734,149 B2 * | 5/2014 | Phan | ...................... | A61C 7/146 433/24 |
| 10,111,734 B2 * | 10/2018 | Bernhard | ........... | A61C 13/0013 |
| 2005/0186524 A1 * | 8/2005 | Abolfathi | ................ | A61C 7/10 433/7 |
| 2007/0071902 A1 * | 3/2007 | Dietrich | ................ | B29C 64/118 427/407.1 |
| 2007/0087300 A1 * | 4/2007 | Willison | .................. | A61C 7/12 433/6 |
| 2008/0171300 A1 * | 7/2008 | Forster | ..................... | A61C 7/10 433/7 |
| 2008/0220388 A1 * | 9/2008 | Weissbach Otte | ........ | A61C 7/10 433/7 |
| 2010/0086890 A1 * | 4/2010 | Kuo | ......................... | A61C 7/08 433/6 |
| 2011/0247214 A1 | 10/2011 | Huge | | |
| 2013/0071802 A1 * | 3/2013 | Lee | .......................... | A61C 7/10 433/7 |
| 2013/0071811 A1 * | 3/2013 | Groscurth | .............. | A61C 1/084 433/75 |
| 2013/0095446 A1 * | 4/2013 | Andreiko | ................. | A61C 7/08 433/6 |
| 2013/0209952 A1 * | 8/2013 | Kuo | ......................... | A61C 7/002 433/10 |
| 2014/0154637 A1 * | 6/2014 | Hansen | ................... | A61C 7/20 433/20 |
| 2015/0157421 A1 * | 6/2015 | Martz | ...................... | A61C 7/08 433/6 |
| 2015/0257856 A1 * | 9/2015 | Martz | ...................... | A61C 7/08 433/6 |
| 2016/0008098 A1 * | 1/2016 | Dolfi | ....................... | A61C 7/10 433/7 |
| 2016/0222793 A1 * | 8/2016 | Snyder | .................... | F01D 5/189 |
| 2017/0007368 A1 * | 1/2017 | Boronkay | ............. | A61C 7/002 |
| 2017/0189140 A9 * | 7/2017 | Kuo | ......................... | A61C 7/08 |
| 2017/0290643 A1 * | 10/2017 | Giardino | ................. | A61C 7/10 |
| 2017/0354482 A1 * | 12/2017 | Kim | ......................... | A61C 7/10 |
| 2017/0367791 A1 * | 12/2017 | Raby | ...................... | A61C 7/002 |

FOREIGN PATENT DOCUMENTS

| | | | | |
|---|---|---|---|---|
| DE | 3831292 A1 | 3/1990 | | |
| DE | 102005049886 A1 | 4/2007 | | |
| DE | 102007014985 A1 | 10/2008 | | |
| FR | 2968926 A1 * | 6/2012 | ............ | A61C 13/01 |
| WO | 2006125072 A2 | 11/2006 | | |
| WO | 2014008583 A1 | 1/2014 | | |
| WO | WO-2014008583 A1 * | 1/2014 | ............... | A61C 7/00 |

* cited by examiner

ORTHODONTIC APPARATUS AND METHOD FOR PRODUCING AN ORTHODONTIC APPARATUS

FIELD OF THE INVENTION

The present invention relates to an orthodontic apparatus and a method for producing an orthodontic apparatus, such as, for example, a dental brace.

BACKGROUND OF THE INVENTION

In a conventional way dental braces are produced in that a physical model of a jaw including the teeth is produced, orthodontically effective elements, such as, for example, wires, are placed on the model and then a hardening plastic is shaped on the model and the elements, which fixes and connects the elements. Then a subsequent adjustment or polishing can be necessary. Such a method is described e.g. in DE 3831292 A1.

For such a method, an impression of the jaw with teeth must first be made on the patient, which impression serves as the negative template for the physical jaw model. For this purpose an impression aid, e.g. an impression tray with molding material, such as, for example, plaster, alginate or silicon, must be introduced into the mouth of a patient, must be pressed on the jaw, and after a period of waiting removed again. This procedure is unpleasant for the patient and time-consuming. Furthermore during the production of the dental brace the individual steps must be carried out successively in several procedures, independently of one another, whereby waiting periods occur in each case. The production of the dental brace is therefore time-consuming and costly. Moreover, during production of the jaw model, during placement of the orthodontic elements and/or during hardening of the plastic, tolerances with respect to the jaw of the patient can arise which make an optimal fit of the dental brace and an optimal effect impossible.

For the production of tooth replacement pieces, imaging methods have been developed, from which a three-dimensional model of the jaw with teeth can be generated. For this purpose, e.g. a camera or a scanner is introduced into the mouth, which photographs or scans the jaw at different pictorial angles. Or, by means of another three-dimensional picture-generating technology, such as e.g. digital volume tomography, computer-assisted tomography or magnetic resonance tomography. From these pictures a computer software can calculate a data set for a virtual jaw model, from which a further data set for the shaping of the tooth replacement piece can be determined. On the basis of this data set the tooth replacement part can be produced, e.g. by means of a rapid prototyping technique. The tooth replacement part is thereby constructed through stepwise hardening of material layers applied on top of one another, e.g. by means of laser radiation. Such methods are described e.g. in DE 102007014985 A1 and DE 102005049886 A1. Tooth replacement pieces, such as, for example, dental crowns, dental bridges or implants, are space-filling single pieces with a volume of several square millimeters. For voluminous parts of this kind, additive methods, such as rapid prototyping, are known from the mechanical production industry.

It is an object of the invention to create an orthodontic apparatus, which is comfortable for a patient to wear, which flawlessly implements an orthodontic treatment, and can be adjusted in a simple way. Furthermore it is an object of the invention to provide a method for producing an orthodontic apparatus, which does not stress the patient very much, can be accomplished with few working steps, is quick and precise, and which makes possible adjustments in a simple way.

This object is achieved by the invention by means of an orthodontic apparatus according to claim 1 and a method for producing an orthodontic apparatus according to claim 6. Advantageous embodiments and further embodiment examples are described in the dependent claims.

BRIEF SUMMARY OF THE INVENTION

An orthodontic apparatus according to the present invention has at least one orthodontically effective element and at least one holding element for holding the apparatus on the jaw. An orthodontically effective element is e.g. a wire bracket, which e.g. abuts on one or more teeth, a jaw plate, which rests on the jaw, an adjustment element for adjusting wire brackets, etc. and other elements, as are common with orthodontic apparatuses. A holding element can be e.g. a tooth support which is placed on or around a tooth in order to fix the apparatus on the jaw. In principle, a holding element can also be an orthodontically effective element. As a rule, the apparatus has a plurality of orthodontic elements and a plurality of holding elements, in order to be able to have an effect individually on different regions in the jaw and to be able to hold the apparatus securely on the jaw.

According to the invention, the orthodontic apparatus is designed in one piece. Understood thereby by the term "in one piece" should be that the entire apparatus with all its elements is formed in one piece. To begin with, there are not any individual pieces or respectively elements which then have to be firmly connected together. The one-piece apparatus thereby has different regions that correspond to the orthodontic elements and the holding elements, and fulfil their function. The different areas merge directly into one another. It is thereby absolutely possible that different regions of the apparatus are made of different materials, for example metal or plastic, which are configured with respect to one another without further connecting means.

In one embodiment of the invention, the orthodontic apparatus comprises at least one wire-type element as an orthodontic element, which extends over a plurality of teeth and is shaped to the contour of the teeth. The shaped wire-type element follows the contour of the teeth in such a way that the element abuts at least for the most part on the outer surface of the teeth. A pressure, which is exerted by the wire-type element on the teeth, can thereby be transmitted over a large area to the teeth, whereby the orthodontic effect can be precisely implemented.

Furthermore in one embodiment of an orthodontic apparatus of the invention, a holding element is designed in such a way that it partially surrounds a tooth and is shaped, or respectively adapted, thereto. Hence an abutment surface of the holding element, at least for the most part, directly abuts the outer surface of a tooth. The holding element thereby adapts itself to the tooth, and a holding force is transmitted to the tooth over a large area. The holding element is preferably of annular design and surrounds the tooth completely.

In still another embodiment of an orthodontic apparatus according to the invention, at least one of the orthodontic elements is designed as adjustment element for adjustment of the apparatus. The adjustment element can be e.g. a screw. The adjustment element does not have to abut the jaw, but can instead be attached to further orthodontic elements.

An orthodontic apparatus according to the invention is preferably produced through a method for producing an orthodontic apparatus according to the present invention. The method according to the invention comprises at least the following steps. An electronic data set for a three-dimensional model of a jaw, to which the apparatus is supposed to be attached, is produced. Then at least one orthodontic element of the apparatus is positioned virtually on the jaw model. The element is thereby disposed on the jaw model through computer simulation. At the same time a shape for the orthodontic element can be determined. Preferably the element will be adapted to the contour of the jaw region on which it is supposed to be disposed. At least one abutment surface, by which the orthodontic element and thus the apparatus abuts on the jaw, thereby follows at least for the most part the jaw contour. Thus during the virtual positioning the orthodontic elements are advantageously shaped with respect to the jaw model. Afterwards an electronic data set for a three-dimensional model of the apparatus is produced. This data set comprises the positioning of the at least one orthodontic element, and, if foreseen for the apparatus, further elements, such as, for example, holding elements. Finally, the apparatus is produced by means of an additive and/or removal production method according to the data set for the apparatus model.

The method according to the invention is advantageous in particular for the production of an orthodontic apparatus as described above. The method can however also be used advantageously for the further development of an existing apparatus and for integration of prefabricated components into an apparatus. The method is suitable for the production of orthodontic apparatuses with the purpose of moving teeth, such as a movement of the teeth on the jaw alone, or a movement of the jaws with respect to one another, or to prevent undesired tooth movements. Produced can be e.g. removable dental braces, retainers and the like, but also elements for fixed apparatuses.

The production and the processing of the electronic data sets is carried out by a computer, which, among other things, has a suitable algorithm for conversion of image data for the jaw into model data and for positioning of elements relative to the jaw model. The image data for the jaw are captured e.g. by a scanner (intraoral or extraoral), a camera, an ionizing or other non-light-based imaging technology (CT, DVT, MRI), as is known from the state of the art. The computer transmits the data set for the apparatus to a control unit of a production facility for additive or removal production methods.

Used as an additive production method is e.g. selective laser melting, selective laser sintering or rapid prototyping. With additive production methods, a three-dimensional object is produced in that individual material layers are applied in a plane corresponding to the shape of the object and are hardened. Thus the object is constructed in layers, whereby the individual layers connect into a whole and the object is formed in one piece. Through a change of the production material, the object can also have regions of different material. An additive production method has the advantage that less material is needed for producing the apparatus. Used as material from which the apparatus is constructed is biologically compatible material, which can be provided in suitable form, in order to develop the individual layers of the apparatus. The material can be e.g. in fluid form or in powder form. Used as metal can be e.g. cobalt chrome or alloys thereof. In an advantageous way, for production of the apparatus, different production materials can be used for different elements and joined together. Wire-type elements of metal and jaw plates of plastic, for example, can thereby be made. Materials can be used for various regions of the apparatus which fulfil, after hardening, differing requirements with respect to elasticity, hardness and the like.

Used as removal production method is e.g. a laser cutting method, whereby material is removed from a blank, in accordance with the three-dimensional model, in order to obtain the desired form.

One advantage of this production method is that the patient is spared the unpleasant impression using alginate, silicon or the like. In addition, the great variability of the shaping by means of the virtual positioning of the elements offers the possibility of designing dental braces for the patient in as pleasant a way as possible. Thickness and rigidity of the elements and of the entire apparatus can be optimally adapted and a perfect accuracy of fit can be achieved for the tooth-dental brace connection.

In a variant of the method according to the invention, a plurality of orthodontic elements of the apparatus are positioned independently of one another, and are integrated in an apparatus model. In the apparatus model the plurality of orthodontic elements are thereby joined together in one piece. Preferably all orthodontic elements and also holding elements for holding the apparatus on the jaw and other elements are positioned on the jaw model, are included in the apparatus data set, and are produced through the additive, or respectively removal, production method. The apparatus can thereby be produced quickly and with an accurate fit.

In another variant of the method according to the invention, one or more pre-dimensioned or prefabricated components, such as e.g. adjustment elements in the form of screws, can be positioned virtually relative to the orthodontic elements, and can be included in the electronic data set for the apparatus model. With the additive production of the apparatus, the production material is then distributed in layers around the component and hardened, so that this component is firmly incorporated into the apparatus. It is thereby also possible that through the radiation, which is used for hardening, the production material bonds chemically with the material of the component. The apparatus can thus be expanded as desired with components e.g. in the form of conventional dental-technical devices.

In still another variant of the method according to the invention, after production of the apparatus, further elements can be added by means of an additive production method and/or existing elements or parts of elements can be removed by means of a removal production method. The apparatus can thereby be adapted to new requirements, or can be corrected after production, if necessary. For this purpose the existing apparatus is included in the data set for the model apparatus, and the further elements are added virtually, or regions are eliminated virtually that are supposed to be removed.

In the method, the apparatus is preferably aligned or disposed during production of the apparatus in such a way that during the arrangement in layers, or respectively during the hardening of the production material, not too great an amount of heat arises in the surroundings of a melting place, which could damage already completed portions of the apparatus.

It is an advantage of the method according to the invention that the apparatus is produced with elements from different metals, such as e.g. cobalt chrome and nickel titanium. This can take place either by adding during the preparation, by direct connection during the creation process or through local changing of the material composition during the production process. Thus, for example, elements like finger springs can be provided on the apparatus. By means of captured 3D data of existing dental braces, e.g. of molar bands, the apparatus can also be connected directly to these, whereby connecting parts are designed corresponding to the shape and are incorporated into the apparatus model. Furthermore the apparatus can be expanded with plastic elements, which are produced either conventionally or by rapid prototyping, such as, for example, lip bumpers with a labial plastic shield. The apparatus can be fixed to skeletal anchors, such as e.g. to a mini implant system.

The invention has been presented with reference to a plurality of examples. The individual technical features of one example can by all means be used also in combination with another example with the explained advantages. The description of the inventive technical features is therefore not limited to the respective example.

Advantageous embodiments of the invention will be presented in the following, with reference to the drawings, which serve merely explanatory purposes and are not to be interpreted in a limiting way. Features disclosed from the drawings should be considered as belonging to the disclosure of the invention individually and in any combination. In the drawings:

DESCRIPTION OF EXAMPLE EMBODIMENTS

Figure 1:
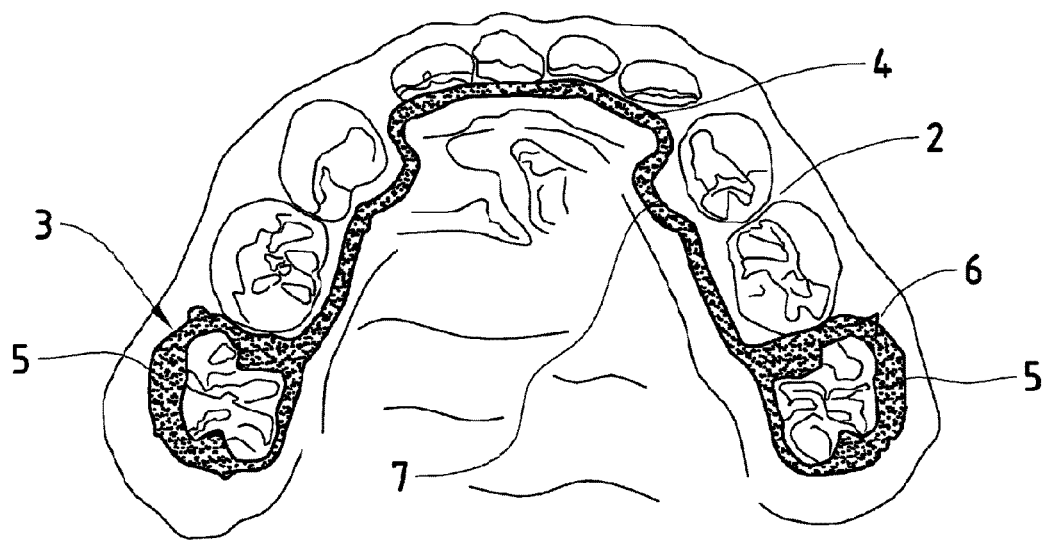
FIG. 1 shows a section of a modelling of a first orthodontic apparatus.
Figure 2:
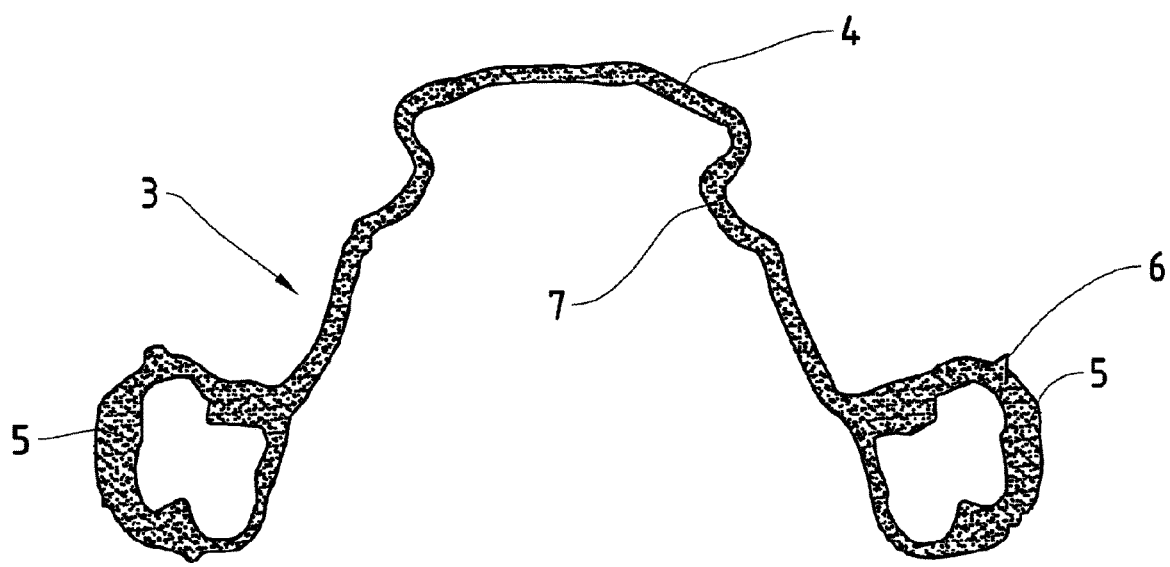
FIG. 2 shows the first orthodontic apparatus from the modelling according to FIG. 1.

FIG. 1 shows a section from an image during the modelling of a first orthodontic apparatus 1, as it is shown in FIG. 2. Shown in FIG. 1 is a picture of a three-dimensional jaw model 2 of a lower jaw with teeth, as determined by means of an electronic data set for the jaw model. The data set was obtained from images taken in the mouth of a patient. Shown furthermore is a three-dimensional model of the apparatus, the apparatus model 3, as determined by means of an electronic data set for the apparatus model. The apparatus model 3 comprises a wire-type orthodontic element 4, which extends on the inside of the jaw along several teeth. The orthodontic element 4 lies on the inner side of the incisors, abutting these, and follows the contour of these teeth in order to support itself on them. The wire-type element 4 further comprises a tension bend 7. The lateral regions of the element 4 along the molars run at a spacing apart from the teeth. Provided on both ends of the orthodontic element 4 is in each case a holding element 5, which surrounds a molar as annular element. The holding elements 5 are situated encircling the tooth with one abutment face on the tooth so that the abutment surface is adapted to the contour of the tooth. The apparatus model shows how the orthodontic element 4 and the holding elements 5 are positioned on the jaw model 2, so that the apparatus is supported on the incisors and the rear molars, and can exert a pressure by means of the tension bend 7. Moreover the holding elements 5 have on their outer surface small protrusions 6, which serve as contact points during release of the apparatus from the jaw.

In principle, it is possible to provide, in addition to the elements foreseen for the apparatus, auxiliary elements which facilitate the production by means of an additive production method. The auxiliary elements are included in the data set for the apparatus model, and are co-produced during the production. The auxiliary elements are subsequently removed, for example through a removal production method. Provided as auxiliary elements can be e.g. crosspieces or braces which connect the right and left jaw sides of the apparatus.

FIG. 2 shows the orthodontic apparatus 1, as it has been produced with the production method according to the invention. The apparatus is made of metal. It is clearly apparent that the apparatus 1 is of one piece. Both the wire-type orthodontic element 4 and the two holding elements 5 are shaped as one piece in a seamless way. By means of the method according to the invention, it is possible to design different regions of the wire-type element 4 with different diameters or cross sections. For example, it is advantageous if the lateral regions and the region at the incisors have an oval cross section, whereby the element is stiffer in these regions, and to provide a round cross section in the region of the tension bend 7, whereby this is more easily bendable. The orthodontic apparatus 1 was produced completely through an additive production method according to the production method of the invention. The apparatus was therefore produced completely in one working process.

Figure 3:
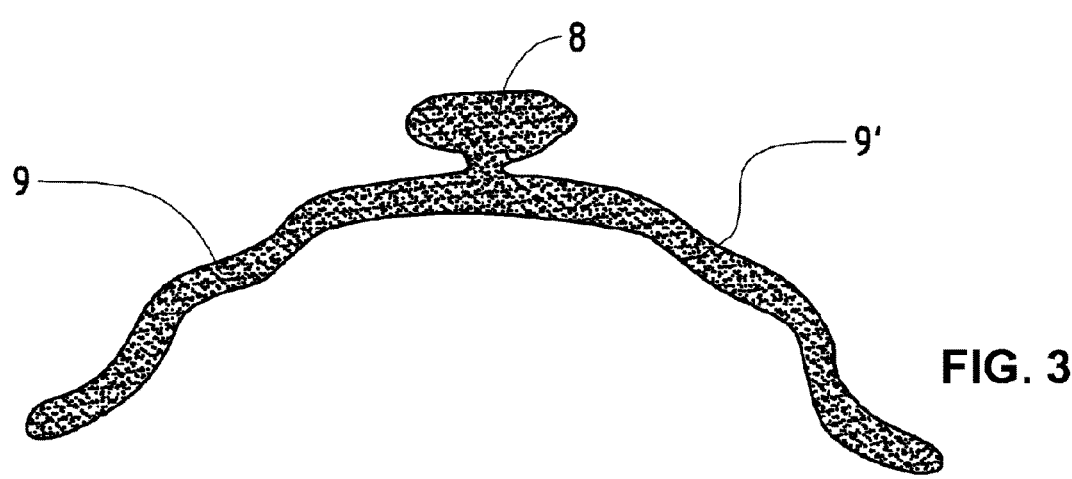
FIG. 3 shows a second orthodontic apparatus in the form of a retainer.

FIG. 3 shows a retainer, which serves to prevent an undesired movement of teeth. The retainer has a holding element 8 and two orthodontic elements 9 and 9' extending on both sides of the holding element 8. The orthodontic elements 9 and 9' are adapted to the contour of the teeth, and keep these teeth in their position. The contact surface to the teeth is in each case flattened for an optimal holding surface so that the diameter between the teeth varies between round and semi-circular at the tooth surfaces. The holding element 8 serves for optimal positioning in the mouth of the patient, and is separated after the fixing to the teeth. The retainer is likewise designed in one piece.

Figure 4:
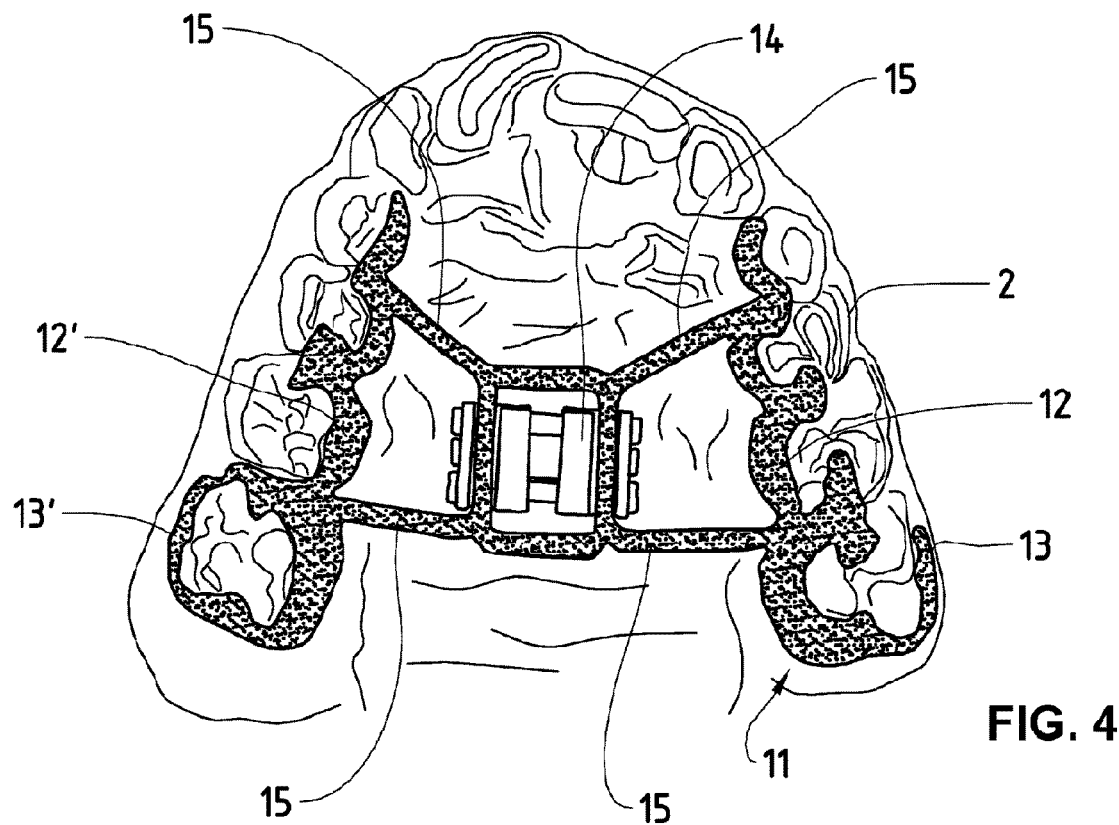
FIG. 4 shows a section of a modelling of a second orthodontic apparatus with an adjustment element.
Figure 5:
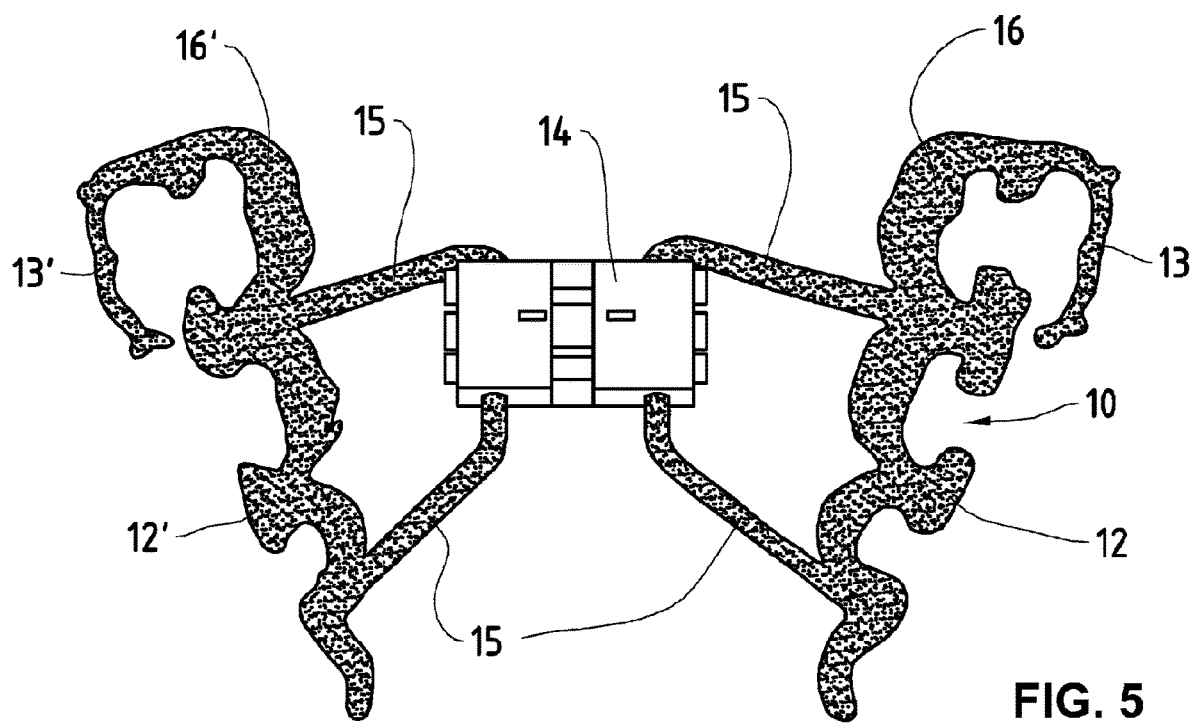
FIG. 5 shows the second orthodontic apparatus from the modelling according to FIG. 4.

FIG. 4 shows a section from an image during the modelling of a second orthodontic apparatus 10, as it is shown in FIG. 5. Shown in FIG. 4 is once again an image of a three-dimensional jaw model 2, in this case an upper jaw. The picture shows an apparatus model 11, which comprises on the right and the left side of the jaw one orthodontic element each 12 and 12', which adapt to the inner side of the molars and follow the contour of the teeth. Around the rearmost molars the orthodontic elements 12 and 12' are provided with holding elements 13 and 13', which run almost completely around the tooth and abut this tooth in a precisely fitting way. The apparatus model 11 further shows an adjustment element 14 in the form of an expansion screw. The adjustment element 14 is connected to the orthodontic elements 12 and 12' by means of wire-type connecting elements 15. The adjustment element 14 is available as a prefabricated component, as is known from the state of the art. A graphic image was made of the component, and the image data obtained therefrom were integrated into the data set for the apparatus model. During the production of the orthodontic apparatus 10 using the method according to the invention, the component for the adjustment screw is taken into account in the method during the additive production process. For this purpose the component is seated at the foreseen position and the layer-wise construction of the apparatus takes place around this component, whereby production material is also joined to the component and is hardened therewith.

FIG. 5 shows the finished orthodontic apparatus 10. Visible in FIG. 5 are contact surfaces 16 and 16' of the orthodontic elements 12 and 12' and of the holding elements 13 and 13', by which the apparatus 10 abuts on the teeth of a patient. It is clearly recognizable that the form of the contact surfaces 16 and 16' corresponds to the contour of the teeth, as they have been determined by the jaw model.

The embodiment of the orthodontic apparatus according to FIGS. 4 and 5 shows an apparatus produced according to the method for producing an orthodontic apparatus according to the present invention. Instead of integrating the adjustment element 14 as a prefabricated component in the apparatus, the adjustment element can be produced according to the invention through the additive production method at the same time with the orthodontic elements 12 and 12' and the connecting elements 15. The orthodontic apparatus produced in this way is designed in one piece. All elements of the apparatus are produced in the same working step. However, it is conceivable e.g. to produce the adjustment screw out of a different production material than the orthodontic elements.

The invention claimed is:

1. An orthodontic apparatus comprising:
an orthodontically effective element comprising a left half and a right half, the left and right halves being integrally formed together with one another as a single piece part together with a holding element for holding the apparatus on a jaw of a user; and
an adjustment element comprising a prefabricated component,
said orthodontically effective element being a wire-type framework comprising left and right wire-type linkages extending from respective tooth-abutting portions thereof to an adjustment element accommodating portion thereof which accommodates the adjustment element, wherein said orthodontically effective element is formed, together with said holding element, of a material that is distributed in layers around the adjustment element and hardened therewith.

2. The orthodontic apparatus according to claim 1, wherein said tooth-abutting portions are configured to extend over a plurality of teeth and are shaped to a contour of the teeth.

3. The orthodontic apparatus according to claim 1, wherein said holding element is configured to be disposed on or at least partially around a tooth.

4. The orthodontic apparatus according to claim 1, wherein said material comprises a plurality of different materials that are used for different regions of the apparatus.

5. The orthodontic apparatus according to claim 1, wherein said material is bonded chemically.

6. The orthodontic apparatus of claim 1, each of the left and right halves of the orthodontically effective element having an area devoid of material, said area being bounded by said left or right respective wire-type linkages, left or right respective further linkages, said respective tooth-abutting portions, and said adjustment element accommodating portion.

7. A method of producing an orthodontic apparatus, the apparatus comprising:
an orthodontically effective element comprising a left half and a right half, the left and right halves being integrally formed together with one another as a single piece part together with a holding element for holding the apparatus on a jaw of a user; and
an adjustment element comprising a prefabricated component;
said orthodontically effective element being a wire-type framework comprising left and right wire-type linkages extending from respective tooth-abutting portions thereof to an adjustment element accommodating portion thereof which accommodates the adjustment element, wherein said orthodontically effective element is formed, together with said holding element, of a material that is distributed in layers around the adjustment element and hardened therewith;
the method comprising the following steps:
producing an electronic data set for a virtual three-dimensional model of a jaw, to which the apparatus is to be attached;
virtual positioning, on the virtual jaw model, of said orthodontically effective element of the apparatus and said holding element for holding the apparatus on the jaw;
virtual positioning of the adjustment element virtually relative to said orthodontically effective element;
producing an electronic data set for a three-dimensional model of the apparatus; and
producing the apparatus by an additive production method according to the data set of the apparatus model.

8. The method according to claim 7, wherein the left half and the right half of the orthodontically effective element are positioned independently of one another and are joined together into an apparatus model.

9. The method according to claim 7, wherein after production of the apparatus further elements are added by an additive production method and/or existing elements or parts of elements are removed by a removal production method.

10. The method according to claim 7, wherein, when producing the apparatus, the apparatus is produced in such a way that with a hardening of consecutive material layers of the additive production method heat arising from already produced portions of the apparatus is shielded or discharged.

11. The method according to claim 7, wherein during the step of producing the apparatus said material comprises a plurality of different materials that are used for different regions of the apparatus.

12. The method according to claim 7, wherein with the virtual positioning of said orthodontically effective element, said orthodontically effective element is shaped on the virtual jaw model.

13. An orthodontic apparatus comprising:
an orthodontically effective element comprising a left half and a right half, the left and right halves being integrally formed together with one another as a single piece part via intermediate crosspieces, at least one of the left and right halves comprising a holding element for holding the apparatus on a jaw of a user; and
an adjustment element comprising a prefabricated component;
said orthodontically effective element being a wire-type framework comprising left and right wire-type linkages extending from respective tooth-abutting portions thereof to an adjustment element accommodating portion thereof which accommodates the adjustment element, wherein said orthodontically effective element is formed, together with said holding element, of a material that is distributed in layers around the adjustment element and hardened therewith, wherein the adjustment element is configured to separate the left and right halves via transmission of separation force through the left and right linkages after removal of said intermediate crosspieces.

\* \* \* \* \*